(12) United States Patent
Van Gompel et al.

(10) Patent No.: US 7,018,368 B2
(45) Date of Patent: *Mar. 28, 2006

(54) PERSONAL CARE ARTICLE HAVING A STRETCH OUTER COVER AND NON-STRETCH GRASPING PANELS

(75) Inventors: Paul Theodore Van Gompel, Hortonville, WI (US); Yung Hsiang Huang, Appleton, WI (US); Georgia Lynn Zehner, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 379 days.

This patent is subject to a terminal disclaimer.

(21) Appl. No.: 10/145,645

(22) Filed: May 14, 2002

(65) Prior Publication Data

US 2002/0138059 A1 Sep. 26, 2002

Related U.S. Application Data

(63) Continuation of application No. 09/002,020, filed on Dec. 31, 1997, now Pat. No. 6,387,085.

(51) Int. Cl.
*A61F 13/15* (2006.01)

(52) U.S. Cl. .......... 604/385.16; 604/389; 604/391; 604/396; 604/387; 604/385.01

(58) Field of Classification Search ............ 604/389, 604/391, 394, 385.01, 396, 387, 386, 385.16
See application file for complete search history.

(56) References Cited

U.S. PATENT DOCUMENTS

| | | | |
|---|---|---|---|
| 4,617,022 A | 10/1986 | Pigneul et al. | 604/391 |
| 4,699,622 A | 10/1987 | Toussant et al. | 604/389 |
| 4,701,170 A | 10/1987 | Wilson et al. | 604/385 |
| 4,704,114 A | 11/1987 | Wilson et al. | 604/385 |
| 4,747,846 A | 5/1988 | Boland et al. | 604/38 A |
| 4,808,176 A | 2/1989 | Kielpikowski | 604/385.2 |
| 4,834,736 A | 5/1989 | Boland et al. | 604/385.2 |
| 4,834,738 A | 5/1989 | Kielpikowski et al. | 604/385.2 |
| 4,834,742 A | 5/1989 | Wilson et al. | 604/389 |
| 4,850,990 A | 7/1989 | Huntoon et al. | 604/385.2 |
| 4,938,753 A | 7/1990 | Van Gompel et al. | 604/385.2 |
| 5,032,122 A | 7/1991 | Noel et al. | 604/391 |
| 5,057,097 A | 10/1991 | Gesp | 604/389 |
| 5,288,546 A | 2/1994 | Roessler et al. | 428/284 |
| 5,399,219 A | 3/1995 | Roessler et al. | 156/259 |
| 5,496,298 A | 3/1996 | Kuepper et al. | 604/389 |
| 5,516,567 A | 5/1996 | Roessler et al. | 428/40.1 |
| 5,542,942 A | 8/1996 | Kline et al. | 604/385.2 |
| 5,554,143 A | 9/1996 | Roe et al. | 604/385.2 |
| 5,575,783 A | 11/1996 | Clear et al. | 604/385.1 |
| 5,593,401 A | 1/1997 | Sosalla et al. | 604/385.2 |
| 5,605,735 A | 2/1997 | Zehner et al. | 428/100 |

(Continued)

FOREIGN PATENT DOCUMENTS

EP 0 721 770 A2 7/1996

(Continued)

*Primary Examiner*—Jacqueline F. Stephens
(74) *Attorney, Agent, or Firm*—David J. Arteman; Alyssa A. Dudkowski

(57) ABSTRACT

A personal care article includes a resiliently stretchable outer cover and a first and second substantially non-stretchable grasping panels attached to the article. The outer cover is resiliently stretchable in at least the cross-direction to conform to the body of a wearer. The absorbent structure is secured to the outer cover by extendible attachment elements.

35 Claims, 5 Drawing Sheets

U.S. PATENT DOCUMENTS

| | | | |
|---|---|---|---|
| 5,624,429 A | 4/1997 | Long et al. | 604/391 |
| 5,683,533 A | 11/1997 | Keighley et al. | 156/204 |
| 5,722,968 A | 3/1998 | Datta et al. | 604/391 |
| 5,846,262 A | 12/1998 | Sayama et al. | 604/391 |
| 5,899,896 A * | 5/1999 | Suprise et al. | 604/391 |
| 6,030,373 A | 2/2000 | Van Gompel et al. | 604/386 |
| 6,045,543 A | 4/2000 | Pozniak et al. | 604/385.1 |
| 6,129,720 A | 10/2000 | Blenke et al. | 604/385.16 |

FOREIGN PATENT DOCUMENTS

| | | |
|---|---|---|
| WO | WO 96/09027 | 3/1996 |

* cited by examiner

PERSONAL CARE ARTICLE HAVING A STRETCH OUTER COVER AND NON-STRETCH GRASPING PANELS

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Personal care articles such as infant diapers, training pants, adult incontinence products, and the like are well known. Such articles have achieved a wide acceptance due to their ability to receive and absorb body exudates.

This invention pertains to non-stretch grasping panels for use with fastener systems for such articles. The grasping panels comprise non-stretch members that assist in proper positioning of fastening tabs with respect to the front edge of such a personal care article. The grasping panels allow a user to stretch the outer cover or substrate of the absorbent article while properly and evenly positioning the grasping panel relative to a respective fastener when mounting the article to the body of a wearer. In some embodiments, the grasping panels are secured to an outer cover. In other embodiments, the grasping panels are secured to a substrate comprising an outer cover and a bodyside liner.

In yet another embodiment, the outer surface of the outer cover comprises a stretch landing zone overlying at least a portion of an absorbent core so that the fastening tabs, when fastened to the outer cover, overlie at least a portion of the absorbent core.

BACKGROUND OF THE INVENTION

In general, personal care articles should comfortably fit the body of a wearer. Personal care articles generally have fastening tabs at the rear of the personal care article that extend outwardly and secure to a front portion of the article. For the personal care article to be effective, the front panels of the article need to be properly placed and maintain their position relative to the fastening tabs, the front waistband, and the rear waistband of the article.

Personal care articles need to be properly fitted to the body of a wearer. In the past there has been little thought or concern as to the positioning of the grasping panels with respect to the body of the wearer and the waistband sections of the personal care article. For standard personal care articles having no stretch in the waistband, except for that caused by waist elastics, known grasping panels tend to maintain their position.

However, when the personal care article has a stretchable outer cover, at least in the front portion thereof, and the grasping panels are integral therewith, or are made of a stretchable material, the grasping panels do not function properly because stretch tends to accumulate at points grasped by the user of the panel, thereby distorting the shape of the grasping panel in the process of securing the personal care article on the wearer.

The invention described herein solves the above problem by providing a substantially non-stretch grasping panel in combination with a stretchable outer cover, thereby permitting more uniform stretch across the entirety of at least the front waistband section of the personal care article. In this manner, the personal care article provides a better fit for the wearer. For example, using the invention, grasping panels of the personal care article are unlikely to roll up, and thus maintain a somewhat planar configuration, when the panels are placed adjacent the body of the user and extended.

The invention also includes locating the landing zone of the personal care article at a location overlying at least part of the absorbent core. As a result, when in use, at least part of the fastening tabs secured to the landing zone overlie the absorbent material. When properly positioned, the landing zone can secure the fastening tabs at an ideal location spaced from the front edge of the article and overlying the absorbent material.

SUMMARY OF THE DISCLOSURE

The present invention relates to a personal care article having a lateral cross-direction and a lengthwise longitudinal direction, a front portion, a rear portion, and a crotch portion interconnecting the front and rear portions. The personal care article comprises a resiliently stretchable outer cover having a first waistband section in the front portion and a second waistband section in the rear portion, the first waistband section being resiliently stretchable along at least the cross-direction and having first and second laterally opposed end regions, the second waistband section having third and fourth laterally opposed end regions, fastener apparatus, for holding the personal care article on a wearer, being disposed at at least one of the front and rear portions on at least one of the first, second, third, and fourth end regions, and a substantially nonelastomeric grasping panel disposed at the other of the front and rear portions on at least one of the respective end regions.

In some embodiments, the fastener apparatus comprises a fastener tab substrate having a first surface and an opposing second surface, at least one fastener component secured to at least a portion of the first surface of the fastener tab substrate, the second surface of the fastener tab substrate being secured to at least a portion of the outer cover at the respective end region, the fastener component being operable to make a fastening attachment to a resiliently stretchable landing zone of the personal care article. The fastener component in its entirety can overlie at least a portion of the first surface of the fastener tab substrate. The fastener component can comprise hook material.

In other embodiments, the fastener component extends outwardly from the fastener tab substrate.

In some embodiments, the fastener component is arranged and configured to make a fastening attachment to a resiliently stretchable landing zone of the personal care article. The landing zone can comprise a nonwoven fabric portion of the outer cover, engageable with the fastener component to provide an operable fastening attachment of the fastener component to the landing zone.

In some embodiments, the personal care article includes an absorbent structure superposed on and operably connected to the outer cover to form an absorbent article. The absorbent structure can include a liquid impermeable backsheet, a liquid permeable bodyside liner superposed on the backsheet, and an absorbent core disposed between the bodyside liner and the backsheet. The personal care article can further comprise extendible attachment elements that secure the absorbent structure to the outer cover while accommodating resilient stretching of the outer cover along the cross-direction.

In some embodiments, the extendible attachment elements accommodate resilient stretching of the first waistband section to at least about 5% elongation, as determined with respect to an unstretched condition of the first waistband section. The extendible attachment elements each have at least one pleat folded therein that connects the absorbent structure and the outer cover.

In some embodiments, the fastener apparatus comprises fastener components secured to a surface of the outer cover at respective end regions and operable to make fastening attachments to a resiliently stretchable landing zone of the personal care article, the landing zone generally overlying the absorbent structure. The fastener components can extend outwardly from the outer cover at the respective end regions.

In preferred embodiments, the grasping panel has a Gurley stiffness value of at least about 10 milligrams. In some embodiments, the grasping panel has a Gurley stiffness value of up to about 10,000 milligrams. In other embodiments, the grasping panel can have a Gurley stiffness value of up to about 2,000 milligrams.

In some embodiments, the second waistband section is resiliently stretchable along the cross-direction.

In some embodiments, the personal care article includes an extensible bodyside liner superposed in surface-to-surface relationship on the outer cover.

In preferred embodiments, the grasping panel has a width of at least about 2 centimeters and a length of at least about 3 centimeters.

In other embodiments of the invention, the personal care article includes an outer cover, at least about 30% of the area of the outer cover being resiliently stretchable, the outer cover having a first waistband section in the front portion and a second waistband section in the rear portion, at least one of the first waistband section and the second waistband section being resiliently stretchable along at least the cross-direction, fastener apparatus for holding the personal care article on a wearer, the fastener apparatus being disposed at at least one of the front and rear portions on at least one of the first, second, third, and fourth end regions, and a substantially nonelastomeric grasping panel disposed in the other of the front and rear portions on at least one of the respective end regions, the grasping panel assisting a user in stretching the outer cover while properly and evenly positioning the grasping panel relative to the fastener apparatus when mounting the personal care article to the body of a wearer.

In other embodiments of the invention, the personal care article comprises an outer cover, at least about 30% of the area of the outer cover being resiliently stretchable, the outer cover having a first waistband section in the front portion and a second waistband section in the rear portion, at least one of the first waistband section and the second waistband section being resiliently stretchable along at least the cross-direction, the first waistband section having first and second laterally opposed end regions and the second waistband section having third and fourth laterally opposed end regions, an absorbent structure superposed on and operably connected to the outer cover and including an absorbent core for receiving and storing exudates, fastener apparatus disposed at at least one of the first and second end regions, or at at least one of the third and fourth end regions for holding the article on a wearer, and a resiliently stretchable landing zone overlying at least a portion of the absorbent core for engagement to the fastener apparatus.

In some embodiments, the grasping panel is secured to at least one of the first, second, third, or fourth end regions by ultrasonic bonding.

In other embodiments of the invention, the personal care article comprises a resiliently stretchable outer cover, the outer cover having a first waistband section in the front portion and a second waistband section in the rear portion, the first waistband section being resiliently stretchable along at least the cross-direction and having first and second laterally opposed end regions, the second waistband section having third and fourth laterally opposed end regions, and a substantially nonelastomeric fastener apparatus being secured to at least one of the first, second, third, and fourth end regions for holding the personal care article on a wearer.

In preferred embodiments, the fastener apparatus has a Gurley stiffness value of at least about 10 milligrams. In most embodiments the fastener apparatus has a Gurley stiffness value of less than about 10,000 milligrams. In some embodiments, the fastener apparatus can have a Gurley stiffness value of less than about 2,000 milligrams.

Figure 1:
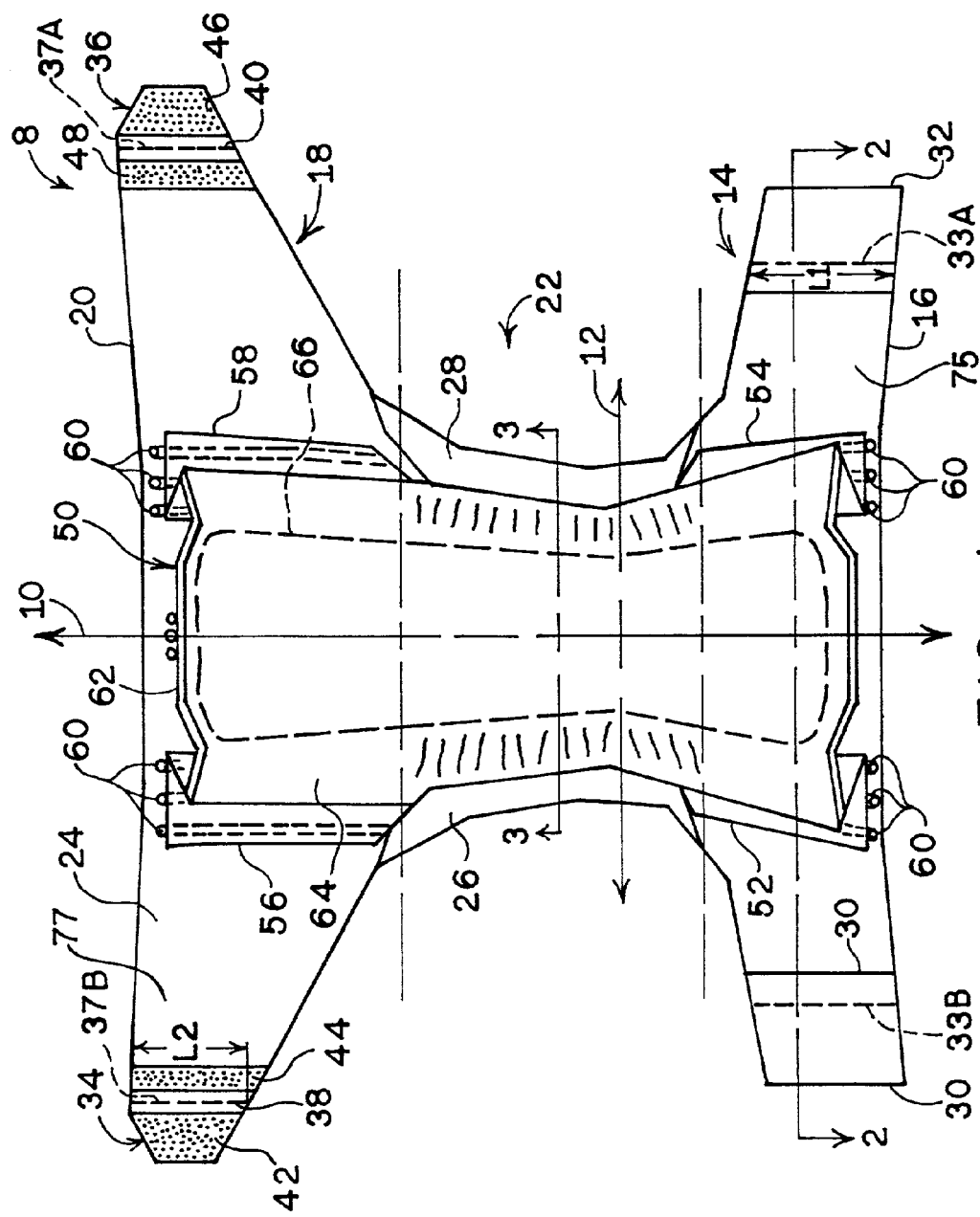
FIG. 1 shows a top view of a first embodiment of personal care articles of the invention.

The invention is not limited in its application to the details of the construction and the arrangement of the components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in disposable personal care articles, but it should be understood that potential uses of the structures of the present invention need not be limited to the context of disposable personal care articles, such as diapers, feminine care articles, incontinence garments, and the like.

As used herein and in the claims that follow, the phrase "personal care article" is meant to include adult incontinence articles, feminine hygiene products, articles which have no significant absorbent function but which receive and/or store urine and/or fecal material, articles which do have a significant absorbent function, and which receive and/or store urine and/or fecal material, such as diapers, training pants, and the like.

Personal care article 8 having a longitudinal axis 10 and a cross-directional axis 12, shown in FIG. 1, includes a front portion 14 having a front edge 16, a rear portion 18 having a rear edge 20, and a crotch portion 22 between front portion 14 and rear portion 18. Longitudinal axis 10 extends in a longitudinal direction through the centers of front portion 14, rear portion 18, and crotch portion 22. Cross-directional axis 12 extends in a cross-direction across the width of personal care article 8. Personal care article 8 includes an outer cover 24. Leg cuffs 26, 28 are located in at least crotch portion 22 of personal care article 8. Leg cuffs 26, 28 preferably provide stretch in the longitudinal direction corresponding to the direction of longitudinal axis 10. Grasping panels 30, 32 are secured to outer cover 24 at opposing end regions 33A, 33B of front portion 14. Fastener apparatus 34, 36 at opposing end regions 37A, 37B of rear portion 18 include respective fastener tab substrates 38, 40, and fastener components 42, 44, 46, 48.

Absorbent structure 50 is superposed on and operably secured to outer cover 24 to form an absorbent article. Absorbent structure 50 includes extendible attachment elements 52, 54, 56, 58 secured by adhesive 60 to portions of outer cover 24.

Figure 2:
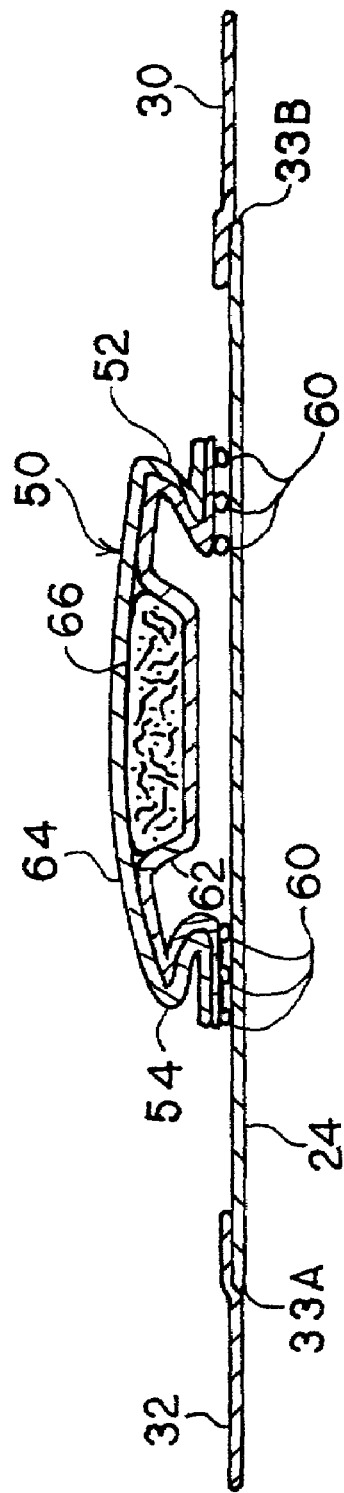
FIG. 2 shows a cross-sectional view of the personal care article of FIG. 1 taken at 2—2.
Figure 3:
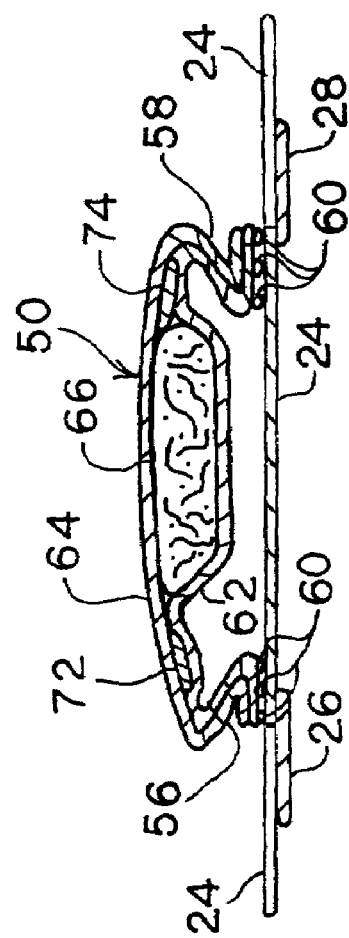
FIG. 3 shows a cross-sectional view of the personal care article of FIG. 1 taken at 3—3.

As better shown in FIG. 2, absorbent structure 50 includes a substantially liquid impermeable backsheet 62, a liquid permeable bodyside liner 64 superposed on backsheet 62, and an absorbent core 66 disposed between backsheet 62 and bodyside liner 64. As better shown in FIG. 1, absorbent structure 50 is secured to outer cover 24 at two locations by extendible attachment elements 52, 54 at least in front portion 14, and at two locations by extendible attachment elements 56, 58 at least in rear portion 18. As shown in FIGS. 2 and 3, extendible attachment elements 52, 54, 56, 58 are extensions of the combination of backsheet 62 and bodyside liner 64 having pleated folds. The pleated folds permit extension of personal care article 8 in the cross-direction without stressing absorbent core 66 or bodyside liner 64.

The cross-section view of FIG. 3 illustrates a zone having elastic elements 72, 74 at opposing sides of absorbent structure 50. Elastic elements 72, 74 preferably are located between and secured to at least one of backsheet 62 and bodyside liner 64 in at least crotch portion 22 of personal care article 8. Elastic elements 72, 74 provide elasticity of absorbent structure 50 in the longitudinal direction. FIG. 3 also shows leg cuffs 26, 28 secured to outer cover 24. Leg cuffs 26, 28 extend longitudinally along opposing outer edges of at least crotch portion 22.

Outer cover 24 preferably comprises a material resiliently stretchable in at least the cross-direction over at least about 30% of the entire surface area of the outer cover from an at-rest condition. Generally, outer cover 24 is resiliently stretchable in at least front portion 14 of personal care article 8. In some embodiments, outer cover 24 can be resiliently stretchable in front portion 14 and rear portion 18 of personal care article 8. Outer cover 24 can also be resiliently stretchable in at least one direction over the entirety of the outer cover.

In other embodiments, outer cover 24 can be resiliently extensible in both the cross-direction and longitudinal direction. Thus, in other embodiments, the entirety of the outer cover can be extended along the direction of both longitudinal axis 10 and cross-directional axis 12 to fit personal care article 8 to a wearer.

Outer cover 24 can include an elastomeric material which provides to the outer cover from about 10% to about 300% elongation within a tension range comfortable to the wearer. In some embodiments outer cover 24 can have an elongation of at least about 30 percent when subjected to a tensile force load of 80 grams per lineal centimeter width of the outer cover transverse to the stretch direction. Outer cover 24 can include a wrap material comprising a film, laminate (film-to nonwoven), a nonwoven elastomer, or a combination thereof. The definition for the phrase "resiliently stretchable" can best be described as the ability of a material to elongate or stretch in response to a force and, after release of the force, to return to substantially its unstretched dimension without significant long term deformation of the material. For example, an exemplary outer cover 24 can be elongated 200% by a force and then return to about 150% of its original length after release of the force.

Elastomers useful in outer cover 24 include thermoplastic elastomers, copolymers and block copolymers (butadienes and the like), polyesters, and ethylene vinyl acetates, and cross-linked and cured elastomers such as rubbers.

The elastomers can be fabricated into continuous or apertured films varying from about 0.2 mils up to about 5 mils in thickness. The elastomers can also be nonwovens or meltblown polymers having basis weights varying from about 5 grams per square meter to about 250 grams per square meter. Composites of elastomers and nonwovens or films can be combined by adhesive, thermal, or ultrasonic bonding of multiple layers to form multiple layer laminates. The outer cover materials can comprise nonwoven materials thermally or otherwise bonded to elastomeric films or meltblown materials such as stretch-bonded laminates or neck-bonded laminates.

An exemplary neck-bonded laminate for outer cover 24 includes a 45 gram per square meter G2755 KRATON® elastomeric film. The film is disposed between, and bonded to, two 23 gram per square meter layers of 40% necked polypropylene spunbonded nonwoven fabrics. Examples of neck-bonded laminates are described in U.S. Pat. No. 5,226,992 issued Jul. 13, 1993 to Morman, the disclosure of which is hereby incorporated by reference in its entirety in a manner that is consistent (not contradictory) herewith.

Outer cover 24 can comprise, for example, suitable meltblown elastomeric fibrous webs as described in U.S. Pat. No. 4,663,220 issued May 5, 1987 to T. Wisneski et al, and hereby incorporated by reference in its entirety in a manner that is consistent (not contradictory) herewith. Composite fabrics comprising at least one layer of a nonwoven material secured to a fibrous elastic layer are well known in the art.

In a particular embodiment wherein outer cover 24 includes an elastomeric material, it is desirable that the outer cover be capable of accommodating an elongation in the cross-direction of at least about 5 percent, more desirably at least about 15 percent, and even more desirably at least about 30 percent when subjected to a tensile force load of 80 grams in the cross-direction per lineal centimeter of the sample measured in the longitudinal direction. Moreover, it is also desirable that outer cover 24 be capable of providing a tension range of from about 20 to about 400 grams, more desirably from about 40 to about 275 grams, and even more desirably from about 60 to about 200 grams per lineal centimeter of the sample measured in the longitudinal direction when subjected to an elongation of 30 percent in the cross-direction.

In another embodiment of the invention, outer cover 24 can be a nonwoven, spunbonded polypropylene fabric composed of, or formed into, a web. The fabric can be creped or necked such that it is extensible in at least one of the longitudinal direction and the cross-direction. Other materials having other advantageous characteristics are also useful as outer cover 24.

In other embodiments, outer cover 24 can comprise a stretch-bonded laminate material having appropriate resilient stretchability. A stretch-bonded laminate comprises at least a two-layered composite in which one layer is a gatherable layer and the other layer a stretchable layer. The layers are joined together when the stretchable layer is in a stretched condition so that, upon relaxing the composite of the joined layers, the gatherable layer is gathered. Other suitable materials also can be utilized for outer cover 24.

Leg cuffs 26, 28 can comprise a laminate of an elastomeric core layer with bicomponent spunbonded facing layers on opposite sides of the elastomeric core layer. The elastomeric core layer may comprise a styrene ethylene butylene styrene terpolymer, such as a KRATON® G polymer from Shell Chemical Company. The elastomeric core layer can be placed between spunbonded facing layers to form a 3-layer stretch-bonded laminate. While a terpolymer is preferred, other polymers such as copolymers can also provide an elastomeric core layer with similar properties.

Leg cuffs 26, 28 preferably are stretchable only in the longitudinal direction. In the alternative, leg cuffs 26, 28 may be stretchable in both the longitudinal and cross directions. Other materials which can form the middle or elastomeric core layer include an elastomeric material or a stretchable meltblown material. For example, a carded web may comprise the elastomeric core layer of leg cuffs 26, 28. Other materials which may comprise the leg cuffs 26, 28 include neck-bonded laminates, or the like. The material forming leg cuffs 26, 28 typically has a maximum elongation of at least about 200% of the relaxed length of the leg cuffs. Other materials having suitable characteristics also can be utilized as leg cuffs 26, 28.

Substantially nonstretchable grasping panels 30, 32 may be formed from a material separate from the outer cover, and then assembled and attached to outer cover 24 at a front waistband section 75. Front waistband section 75 extends inward from front edge 16 in the cross-direction across part of front portion 14. The width of front waistband section 75, inward of front edge 16, corresponds to the length "L1" of the attachment area between grasping panels 30, 32 and outer cover 24. Grasping panels 30, 32 extend outwardly from outer cover 24 to form a pair of opposed waist flap sections. Grasping panels 30, 32 assist a user in applying personal care article 8 to the body of the user.

Grasping panels 30, 32 preferably are secured to outer cover 24 by ultrasonic bonding. Grasping panels 30, 32 can also be secured to outer cover 24 by adhesives, stitching, thermal bonding, clips, staples, solvent bonding or the like.

Grasping panels 30, 32 comprise substantially nonstretchable material, such as substantially non-stretchable polymer films, woven fabrics, non-woven fabrics, or the like, as well as combinations thereof. Preferably, the substantially non-stretchable material of grasping panels 30, 32 is effectively free of fastening properties associated with either of fastener apparatus 34, 36 and the landing zone of the absorbent article.

In some embodiments grasping panels 30, 32 have widths of at least about 2 centimeters and lengths of at least about 3centimeters. Generally, grasping panels 30, 32 can have widths of at least about 4% of the overall length of personal care article 8 and lengths of at least about 7% of the overall length of the respective personal care article.

Grasping panels 30, 32 are formed from materials having a Gurley stiffness of less than about 10,000 milligrams. Preferably, grasping panels 30, 32 have a Gurley stiffness value of less than about 2,000 milligrams, and most preferably, less than about 600 milligrams. Grasping panels 30, 32 can be composed of materials having a Gurley stiffness value of at least about 10 milligrams, preferably at least about 100 milligrams, and most preferably, at least about 200 milligrams.

A suitable method for determining Gurley stiffness values is set forth in TAPPI Standard Test T 543 OM-94. A suitable testing apparatus is a Gurley Digital Stiffness Tester Model 4171-D manufactured by Teledyne Gurley of 514 Fulton Street, Troy, N.Y.

Having a proper Gurley stiffness value for grasping panels 30, 32 is important because, if the stiffness value is too low, excessive wrinkling, necking down, or folding over of the grasping panel can occur when the grasping panels are grasped and pulled away from each other in the process of mounting personal care article 8 on the wearer. Likewise, if the Gurley stiffness values for grasping panels 30, 32 are too large, the grasping panels are rigid and uncomfortable to the body of the wearer. Therefore, the above range of values for Gurley stiffness is preferred in the materials of grasping panels 30, 32.

In some embodiments of the invention, separate stress beam elements (not shown) can be provided at the area of bonding between each grasping panel 30, 32 and outer cover 24. Such stress beam elements can overlie and reinforce the bonding area. Such separate elements can disperse and dissipate the fastening forces across the length of respective grasping panels 30, 32. In addition, a stress beam element can provide additional stiffening and reinforcement of the waistband section. The stress beam element can be a doubled over section of a respective grasping panel. Such a stress beam element is disclosed in U.S. patent application Ser. No. 08/168,615 to T. Roessler et al, entitled Dynamic Fitting Diaper, filed Dec. 16, 1993, the entire disclosure of which is hereby incorporated by reference in a manner that is consistent herewith.

Fastener apparatus 34, 36 may be formed from separate materials that are then assembled and attached to outer cover 24 at a rear waistband section 77. Fastener apparatus 34, 36 can comprise a substantially nonelastomeric fastener material. The rear waistband section extends inward from rear edge 20 and along the cross-direction across part of rear portion 14. The width of rear waistband section 77, inward of rear edge 20, corresponds to the length "L2" of the attachment area between fastening apparatus 34, 36 and outer cover 24. Fastening apparatus 34, 36 extend outwardly from outer cover 24 to form a pair of opposed fastening sections. Fastening apparatus 34, 36 secure to front portion 14 and thus retain personal care article 8 on the body of the user.

Fastener apparatus 34, 36 can be permanently secured to outer cover 24 by ultrasonic bonding. Fastener apparatus 34, 36 also can be irreleasably affixed to outer cover 24 by adhesives, stitching, thermal bonding, clips, staples, solvent bonding or the like.

Fastener apparatus 34, 36 include respective fastener tab substrates 38, 40. Fastener components 42, 44 are secured in surface-to-surface relationship to a single surface of tab substrate 38. Likewise, fastener components 46, 48 are secured in surface-to-surface relationship to a single surface of tab substrate 40.

Fastener apparatus 34, 36 generally are formed by material or materials having a Gurley stiffness of less than about 10,000 milligrams. Preferably, fastener apparatus 34, 36 have a Gurley stiffness value of less than about 2,000 milligrams, and most preferably, less than about 800 milligrams. Fastener apparatus 34, 36 can be composed of materials having a Gurley stiffness value of at least about 10 milligrams, preferably at least about 150 milligrams, and most preferably, at least about 200 milligrams.

Having a proper Gurley stiffness value for fastener apparatus 34, 36 is important because, if the stiffness value is too low, excessive wrinkling, necking down, or folding over of the fastener apparatus can occur when the fastener apparatus 34, 36 are manipulated in the process of mounting the personal care article on the wearer. Likewise, if the Gurley stiffness values for fastener apparatus 34, 36 are too large, the fastener apparatus become rigid and uncomfortable to the body of the wearer. Therefore, the above range of values for Gurley stiffness are preferred in the materials of fastener apparatus 34, 36.

Fastener tab substrates 38, 40 of fastener apparatus 34, 36 can comprise nonwoven material, such as spunbond-meltblown-spunbond material (SMS). Spunbond-meltblown-spunbond material comprises a layer of meltblown material located between and in surface-to-surface relationship with opposing spunbond layers. Such SMS material generally forms fastener apparatus 34, 36 that are substantially non-extensible during normal usage.

Other materials having suitable characteristics can be substituted for the above described tab substrates 38, 40. For example, extensible materials can be utilized for tab substrate. Examples of suitable extensible materials are described in U.S. Pat. No. 5,226,992 issued Jul. 13, 1993, to Morman, the disclosure of which is hereby incorporated by reference in its entirety in a manner that is consistent (not contradictory) herewith.

Fastener components 42, 44, 46, 48 may include flexible hook components, mounted in surface-to-surface relationship to a surface of the respective fastener tab substrates 38, 40 using a layer of adhesive. Other known methods of mounting fastener components 42, 44, 46, 48 to the respective tab substrates 38, 40 may be utilized. Such known methods include, but are not limited to, adhesives, ultrasonic bonding, stitching, thermal bonding, clips, staples, solvent bonding, or other conventional methods.

Figure 4:
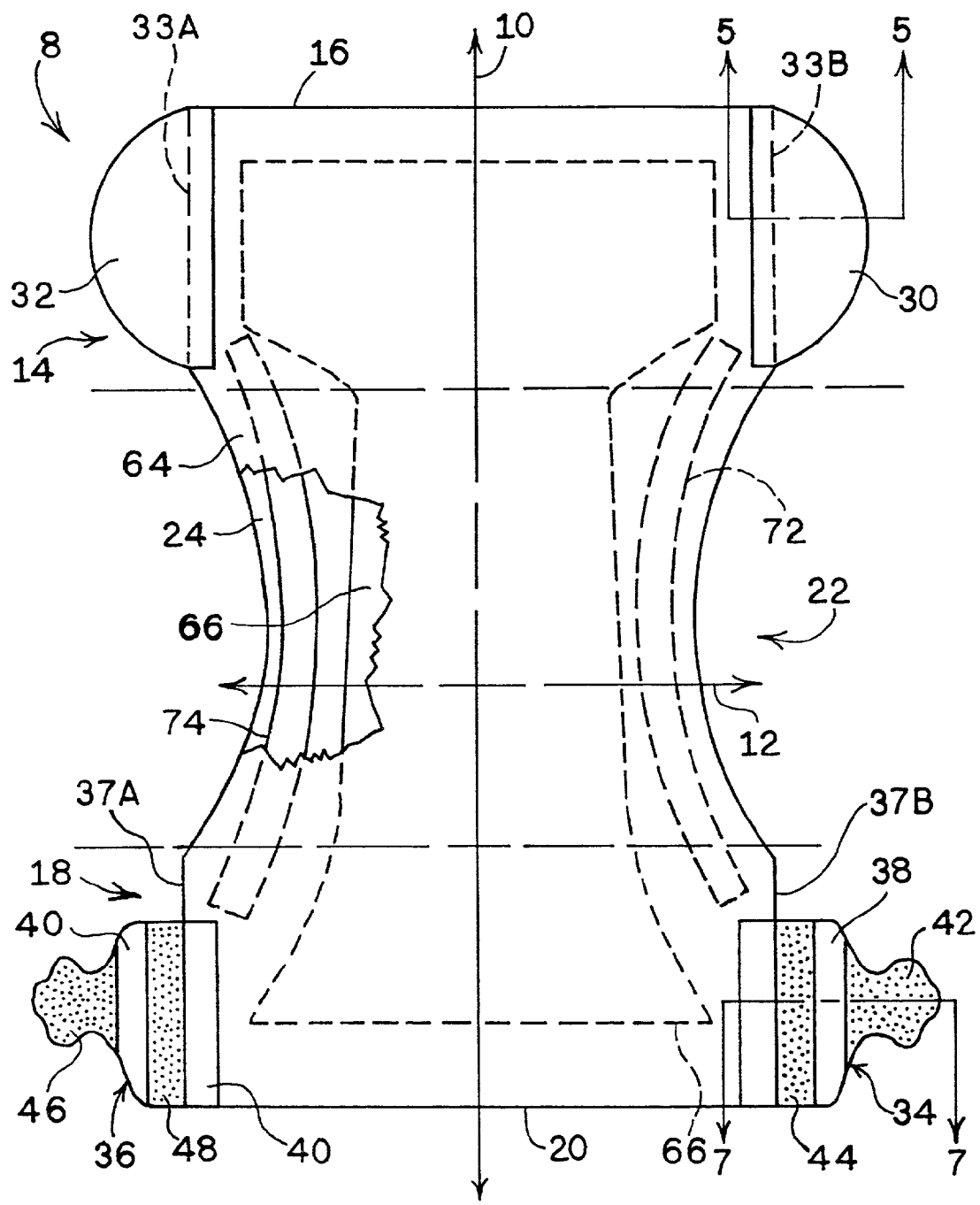
FIG. 4 shows a top view of a second embodiment of personal care articles of the invention having a bodyside liner overlying substantially the entirety of the outer cover.

Fastener components 42, 46 overlie and preferably generally follow the contour of tab substrates 36, 38, especially at respective outside edges of the fastener apparatus 34, 36. Other shapes, of course, are contemplated for fastener apparatus. The fastening apparatus shapes shown in FIGS. 1 and 4 are merely for purposes of illustration, and other shapes are possible and intended.

In use, fastener components 42, 44, 46, 48 are secured to a resiliently stretchable landing zone which is affixed to front portion 14 of outer cover 24, thereby securing the respective fastener apparatus 34, 36 to the resiliently stretchable landing zone of front portion 14. Another example of a fastener apparatus suitable for use in the subject invention is set forth in U.S. Pat. No. 5,399,219 issued Mar. 21, 1995 to Roessler et al, the disclosure of which is hereby incorporated by reference in its entirety in a manner that is consistent (not contradictory) herewith.

Other well known fastener components 42, 44, 46, 48 can be used to support personal care article 8 on the user. For example, a cohesive fastener system, an adhesive fastener system, or the like may be utilized as fastener components 42, 44, 46, 48 with suitable cooperating elements on front portion 14, as necessary, to support personal care article 8 on the wearer.

Preferably, outer cover 24 comprises a material having suitably looped construction such that hooks of fastener components 42, 44, 46, 48 engage directly to the fabric of outer cover 24. Thus outer cover 24 preferably acts as a landing zone for fastener apparatus 34, 36 by functioning as a fastener-receptive area which is integral with outer cover 24. Such an arrangement controls the number of elements that must be formed, placed, and secured on personal care article 8. Therefore the arrangement controls the cost of producing personal care article 8.

Fastener components 44, 48 are optional elements. Namely, in some embodiments, a single fastener component 42, 46 can be used to secure each fastener apparatus to front portion 14 of outer cover 24.

Absorbent structure 50 includes liquid impermeable backsheet 62, permeable bodyside liner 64, absorbent core 66, elastic elements 72, 74, and extendible attachment elements 52, 54, 56, 58 comprising a combination of sections of backsheet 62 and bodyside liner 64.

Extendible attachment elements 52, 54, 56, 58 comprise outwardly extending sections of backsheet 62 and bodyside liner 64 extending outwardly at opposing sides of the front and rear of absorbent structure 50 as shown in FIGS. 1–3. Extendible attachment elements 52, 54, 56, 58 each have a folded or pleated section. The extendible attachment elements are secured by adhesive 60 to outer cover 24. Thus extendible attachment elements 52, 54, 56, 58 secure absorbent structure 50 to outer cover 24 while accommodating resilient stretching of the outer cover along at least the cross direction. Extendible attachment elements 52, 54, 56, 58 accommodate resilient stretching of first waistband section 75 of at least about 5%, as compared to an unstretched condition of the first waistband section. Extendible attachment elements 52, 54, 56, 58 have at least one pleat folded therein connecting absorbent structure 50 and outer cover 24. The pleat or pleats open and extend when personal care article 8 is extended in the cross-direction. Thus extendible attachment elements 52, 54, 56, 58 generally isolate absorbent structure 50 from modest amounts of movement of outer cover 24, thereby to accommodate extensibility of at least front portion 14, of the outer cover, in the cross-direction.

In the embodiment of FIG. 1, the combination of backsheet 62 and bodyside liner 64 can have limited or no extensibility. The pleats of extendible attachment elements 52, 54, 56, 58 can open and unfold sufficiently to accommodate stretching of outer cover 24 in the cross-direction for securement to a wearer.

Extendible attachment elements 52, 54, 56, 58 can comprise a separate element (not shown) secured to at least one of backsheet 62 and bodyside liner 64. Materials suitable for use in separate extendible attachment elements 52, 54, 56, 58 include polyester, foams, and natural fibers. Various other woven and nonwoven fabrics can be used in extendible attachment elements 52, 54, 56, 58. Besides having pleats, extendible attachment elements can comprise extensible elements that stretch or extend significantly in the cross-direction.

Liquid impermeable backsheet 62 can comprise a single layer, or multiple components, layers, or partial layers, of material, such that the resulting backsheet is substantially impermeable to liquids. A typical backsheet 62 may be manufactured from a thin plastic film or other flexible liquid-impermeable material. For example, impermeable backsheet 62 can be formed from a polyethylene film, or a polyethylene film laminated to a surface of a nonwoven web, such as a spunbonded web of polyolefin fibers. Further, liquid impermeable backsheet 62 can be formed of a woven or nonwoven fibrous web which has been totally or partially constructed or treated to impart a desired level of liquid impermeability to selected regions that are adjacent or proximate absorbent core 66. Still further, liquid impermeable backsheet 62 may optionally be composed of a microporous material which permits vapors to escape from absorbent core 66 while preventing liquid exudates from passing through the backsheet.

Bodyside liner 64 includes a skin-facing surface which is compliant, soft-feeling, and non-irritating to the wearer's skin. Further, bodyside liner 64 should be sufficiently porous to be liquid permeable, permitting liquid to penetrate through its thickness.

Bodyside liner 64 may be composed of a substantially hydrophobic and substantially nonwettable material, with the hydrophobic material preferably being treated with a surfactant or otherwise processed to impart a desired level of wettability and hydrophilicity.

Bodyside liner 64 may be manufactured from a wide selection of web materials, such as porous foams, reticulated foams, apertured plastic films or natural or synthetic fibers. For example, bodyside liner 64 may comprise wood or cotton fibers. Other useful materials are synthetic fibers, such as polyester or polypropylene fibers, or a combination of natural and synthetic fibers. Bodyside liner 64 is suitably utilized to help isolate, from the wearer's skin, the liquids held in absorbent core 66.

Various woven and nonwoven fabrics can be used for bodyside liner 64. For example, bodyside liner 64 may be composed of a meltblown or spunbonded web of polyolefin fibers. Bodyside liner 64 may also comprise a carded and/or bonded web composed of natural and/or synthetic fibers.

In a particular embodiment of the present invention, bodyside liner 64 may comprise a spunbonded polypropylene fabric composed of about 2.8–3.2 denier fibers formed into a web having a basis weight of about 22 grams per square meter and a density of about 0.06 grams per cubic centimeter. A preferred fabric is treated with about 0.3 weight percent of a surfactant.

Bodyside liner 64 can be formed from a single layer, or may comprise a multiplicity of components, layers, or partial layers, which correspond to any of the materials disclosed herein for the bodyside liner, as well as others known in the art.

Absorbent core 66, when used in personal care articles 8 of the invention, may be manufactured from a wide variety of materials in a wide variety of sizes, and in a wide variety of shapes such as rectangular, trapezoidal, T-shape, I-shape, hourglass shape, etc. The size, and absorbent capacity of absorbent core 66 should be compatible with the size of the intended wearer and the anticipated liquid loading imparted by the intended use of the absorbent core.

Absorbent core 66 suitably comprises a matrix of hydrophilic fibers, such as a web, or webs, of cellulosic fluff, preferably in combination with a high-absorbency material commonly known as superabsorbent material. In a preferred embodiment, absorbent core 66 comprises a mixture of superabsorbent hydrogel-forming material and wood pulp fluff. In place of the wood pulp fluff, one may use synthetic, polymeric, or meltblown or natural fibers or a combination of wood pulp fluff, synthetic fibers, polymeric fibers, meltblown fibers, and/or natural fibers. The superabsorbent material may be substantially homogeneously mixed with the hydrophilic and/or hydrophobic fibers, or other materials, or may be otherwise combined into absorbent core 66.

Absorbent core 66 may comprise a laminate of fibrous webs and superabsorbent material, or may comprise other suitable structure operative to maintain superabsorbent material fixed in position at desirable locations in the absorbent body.

The high-absorbency material in absorbent core 66 can be selected from natural, synthetic and/or modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Optional elastic elements 72, 74 provide resilient stretchability or additional resilient stretchability in the longitudinal direction for absorbent structure 50. Elastic elements 72, 74, as shown in FIG. 3, are located between bodyside liner 64 and backsheet 62. Materials suitable for forming elastic elements 72, 74 include LYCRA® strands, ribbons, or one or more layers of a polymeric and/or elastomeric material which may be adhered in personal care article 8, thereby forming resilient stretch in crotch portion 22, while the elastic elements are in a stretched condition.

In some embodiments, opposing left and right spaced containment flaps (not shown) can extend longitudinally along the length of personal care article 8 inwardly of respective side edges of the personal care article. In such embodiments, the containment flaps are typically secured to bodyside liner 64. One example of containment flaps is set forth in U.S. Pat. No. 4,704,116 issued Nov. 3, 1987 to K. Enloe, the disclosure of which is hereby incorporated by reference in its entirety in a manner that is consistent (not contradictory) herewith.

Containment flaps may, for example, be constructed of a fibrous material which is similar to the material comprising backsheet 62. Other suitable conventional materials, such as polymeric films, may also be employed.

In use, personal care article 8, shown in FIG. 1, conforms to the body of a wearer, in part, due to resilient stretchability in the cross direction in at least a part of front portion 14 of the article. Grasping panels 30, 32 are pulled away from each other, providing uniform tension so that the front waistband section pulls evenly across at least part of front portion 14 as the grasping panels are wrapped toward the rear of the wearer. Grasping panels 30, 32 have sufficient Gurley stiffness values to control front portion 14 of personal care article 8 and prevent roll-up or wrinkling either of the grasping panels or the personal care article. Then fastener apparatus 34, 36 are extended to and about the front of the wearer, and then are secured to front portion 14 of personal care article 8. Thus personal care article 8 is uniformly fitted and secured to a wearer because of the stretchability of outer cover 24 and the stiffness of grasping panels 30, 32.

FIG. 4 shows a second embodiment of the invention. In this embodiment, absorbent structure 50 is replaced with a more conventional arrangement. Bodyside liner 64 is secured in surface-to-surface relationship with outer cover 24 generally about the outer edges of the outer cover and the bodyside liner. Elastic elements 72, 74 are illustrated on opposing sides of crotch portion 22. The elements illustrated in FIG. 4 have a similar function to the same elements shown in FIG. 1. Further, the elements shown in FIG. 4 can be made of the same materials as described earlier.

As representatively shown in FIG. 4, bodyside liner 64 and outer cover 24 may be generally coextensive and may have length and width dimensions which are generally larger than the dimensions of absorbent core 66. In the illustrated embodiment, bodyside liner 64 is associated with and generally superimposed over the entirety of the surface of outer cover 24, the combination of the outer cover and the bodyside liner thereby mutually defining the periphery of personal care article 8. Absorbent core 66 is optionally disposed between outer cover 24 and bodyside liner 64 inboard of the periphery of personal care article 8.

As in the earlier described embodiment, outer cover 24 is resiliently extensible in at least the cross-direction at at least front portion 14. However, unlike the earlier embodiment, in FIG. 4, bodyside liner 64 is at least extensible in the cross-direction at at least front portion 14. Such an arrangement is necessary to allow front portion 14, containing absorbent core 66, to expand or stretch in at least the cross direction. Such extensibility of bodyside liner 64 may be a function of extensibility of the material used in the bodyside liner, or may be a function of the size and shape of the bodyside liner.

Fastener apparatus 34, 36 can be formed as an integral part of outer cover 24 and/or bodyside liner 64. Such an arrangement reduces the number of elements needed to form personal care article 8.

In the embodiment of FIG. 4, bodyside liner 64 can be, for example, a nonwoven, spunbonded polypropylene fabric composed of fibers formed into a web. The fabric can be creped or necked such that it is extensible in at least one of the cross-direction and the longitudinal direction. Bodyside liner 64 can also comprise a stretch-bonded laminate having appropriate elasticity and width to create general overall surface contact between generally the entirety of the body-facing side of personal care article 8 and the body of a wearer. The stretchable layer can be a stretchable film of stretchable material, such as a layer of styrene ethylene butylene styrene copolymer or other elastomeric polymer, or a plurality of strands of a stretchable material such as latex or LYCRA®. Other materials with similar properties may also, in the alternative, be provided integral with or attached to bodyside liner 64 to thereby impart the stretch properties. All materials should not, however, interfere with the soft texture of bodyside liner 64 against the skin of a wearer.

As shown in FIG. 4, absorbent core 66 extends near front edge 16 such that when fastener apparatus 34, 36 are secured to front portion 14, the fastener apparatus overlie the absorbent core. Such an arrangement maximizes the amount of absorbent core material that can store exudates in front portion 14 of personal care article 8.

Figure 5:
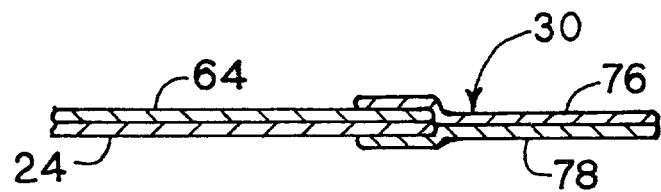
FIG. 5 shows a cross-sectional view of the personal care article of FIG. 4 taken at 5—5.

FIG. 5 shows an embodiment where grasping panels 30, 32 comprise two layers of material 76, 78 secured in surface-to-surface relationship with each other and on opposing sides of outer cover 24 and bodyside liner 64, whereby outer cover 24 and bodyside liner 64, in combination, comprise a substrate for receiving layers 76, 78. Layer 76 of grasping panel 30 extends over a portion of the body facing side of bodyside liner 64 and is secured thereto. Layer 78 extends over a portion of the outwardly facing side of outer cover 24. The layers 76, 78 are bonded to each other and to outer cover 24 as well as to bodyside liner 64. Thus grasping panel 30 is formed by two layers 76, 78.

Figure 6:
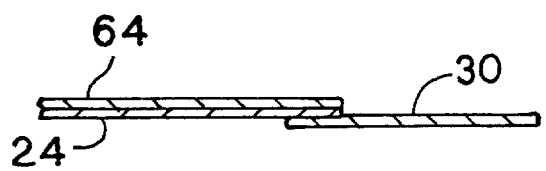
FIG. 6 shows a cross-sectional view of an end region and fastener of a third embodiment of personal care articles of the invention similar to the personal care article of FIG. 4.

FIG. 6 shows a cross-section view of a third embodiment of the invention where grasping panel 30 comprises a single layer of material secured to a portion of the outward facing surface of outer cover 24. In another embodiment (not shown) grasping panel 30 can be secured to the body facing surface of bodyside liner 64.

Figure 7:
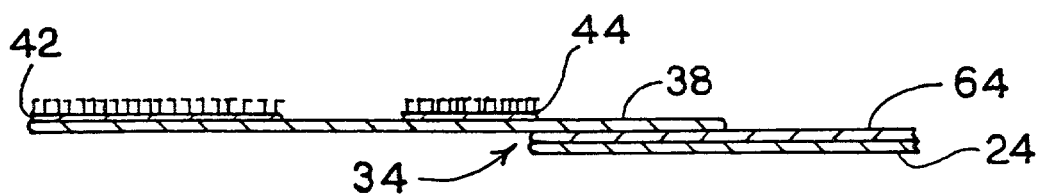
FIG. 7 shows a cross-sectional view of the personal care article of FIG. 4 taken at 7—7.

FIG. 7 shows a cross-section view of personal care article 8 taken at 7—7 of FIG. 4. Fastener apparatus 34 includes fastener tab substrate 38 having a first surface and a second opposing surface. The second surface of fastener tab substrate 38 is secured to bodyside liner 64. Securement can be by ultrasonic bonding, adhesives, or other known techniques. Fastener components 42, 44 are secured to the first surface of fastener tab substrate 38 by other methods. Fastener components 42, 44 can comprise hook material as shown in FIG. 7. As described in earlier embodiments, other types of fastener components may be utilized. In this embodiment, fastener component 42 generally follows the contour of the outer edge of fastener tab substrate 38. Thus fastener component 42, as illustrated in the embodiment of FIG. 7, does not extend outwardly beyond the outer edge of fastener tab substrate 38.

Figure 8:
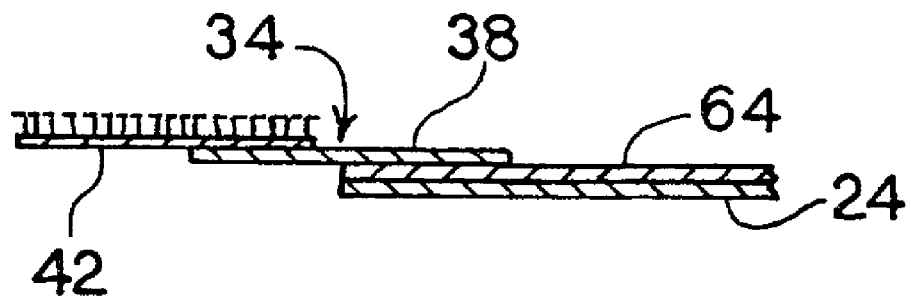
FIG. 8 shows a cross-section view of an end region and fastener of another embodiment of personal care articles similar to the personal care article of FIG. 4.

FIG. 8 shows a cross-section view of another embodiment of the invention of FIG. 4 where fastener apparatus 34 comprises fastener component 42 secured to a portion of a first surface of fastener tab substrate 38 and extending outwardly therefrom in the cross-direction. At least a portion of a second surface of fastener tab substrate 38 is secured to bodyside liner 64. In this embodiment, the portion of fastener component 42 extending outwardly from fastener tab substrate 38 has a much lower Gurley stiffness than the Gurley stiffness of the combined inboard portions of fastener component 42 and fastener tab substrate 38 to which it is secured. In other embodiments, at least a portion of fastener tab substrate 38 can be secured to outer cover 24 instead of bodyside liner 64. In some modifications of the embodiment of FIG. 1, fastener apparatus 34, 36 are always secured to outer cover 24.

Figure 9:
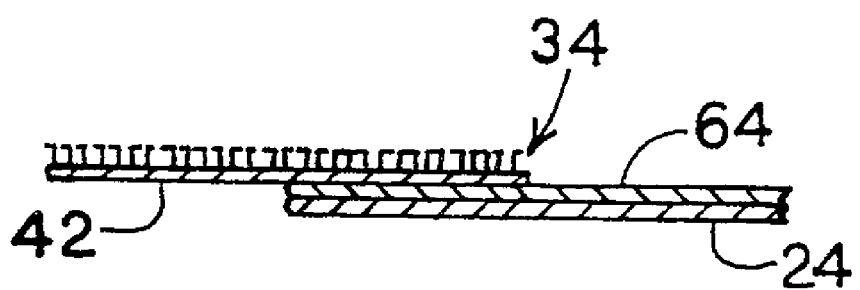
FIG. 9 shows a cross-section view of an end region and fastener of yet another embodiment of personal care articles similar to the personal care article of FIG. 4.

FIG. 9 shows a cross-section view of another embodiment of the invention of FIG. 4 where fastener apparatus 34 comprises a fastener component 42 secured directly to at least a portion of bodyside liner 64. At least a portion of fastener component 42 can extend outwardly of bodyside liner 64. In other embodiments, at least a portion of fastener component 42 can be secured to outer cover 24 instead of to bodyside liner 64. For example, in the embodiment of FIG. 1, fastener component 42 can be directly secured to, and on either surface of, outer cover 24.

The embodiments of FIGS. 4–9 operate in a similar manner to the embodiment of FIGS. 1–3. As described earlier, bodyside liner 64 requires a minimal amount of extensibility in the cross-direction in at least front portion 14.

In other embodiments (not shown), elastic elements 72, 74 can be omitted from personal care article 8 of FIG. 4. Outer cover 24 and bodyside liner 64 can comprise materials extensible in both the longitudinal direction and the cross direction. At least one of outer cover 24 and bodyside liner 64 includes resiliently extensible material that returns to substantially its original position after the removal of force therefrom.

In other embodiments (not shown), fastener apparatus 34, 36 can be located at opposing end regions 33A, 33B in front portion 14 and grasping panels 34, 36 can be located at opposing end regions 37A, 37B in rear portion 18 of personal care article 8.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, such is not meant to include there, or in the instant specification, anything not structurally equivalent to what is shown in the embodiments or otherwise disclosed in the specification.

Having thus described the invention, what is claimed is:

1. A personal care article having a lateral cross-direction and a lengthwise longitudinal direction, a front portion, a rear portion, and a crotch portion interconnecting said front and rear portions, said personal care article comprising:
   (a) an article substrate comprising an outer cover and a bodyside liner, said substrate having a first waistband section in said front portion and a second waistband section in said rear portion, at least one of said first waistband section and said second waistband section being resiliently stretchable along at least said crass-direction, said first waistband section having first laterally opposed end regions and said second waistband section having second laterally opposed end regions;
   (b) an absorbent structure comprising an absorbent core disposed between said outer cover and said bodyside liner, said absorbent core being operable for receiving and storing exudates;
   (c) extendible attachment elements securing said absorbent structure to said outer cover while accommodating resilient stretching of said outer cover along the cross-direction, wherein said extendible attachment elements accommodate resilient stretching of at least one of said first waistband section and said second waistband section, of at least about 5% elongation, as determined with respect to an unstretched condition of the respective said waistband section;
   (d) fastener apparatus configured to hold said personal care article on a wearer, said fastener apparatus being disposed at each laterally opposed end regions of one of said first and second waistband sections;
   (e) first and second substantially non-stretchable grasping panels effectively free of fastening properties, and disposed at said laterally opposed end regions of the other of said first and second waistband sections, whereby said non-stretchable grasping panels are attached to said substrate at portions of said substrate which are stretchable in the cross-direction; and
   (f) a fastener landing zone disposed between said first and second grasping panels, at said outer cover, for receiving and securing said fastener apparatus thereto.

2. A personal care article as in claim 1, further comprising a resiliently stretchable landing zone, wherein said fastener apparatus on each said laterally opposed end region of one of said first and second waistband sections comprises:
   a fastener tab substrate having a first surface and an opposing second surface; and
   at least a first fastener component secured to at least a portion of said first surface of said fastener tab substrate, and said second surface of said fastener tab substrate being secured to said article substrate, said first fastener component being operable to make a fastening attachment to said resiliently stretchable landing zone of said personal care article.

3. A personal care article as in claim 2 wherein at least a portion of said first fastener component extends outwardly from said fastener tab substrate.

4. A personal care article as in claim 2 wherein an entirety of said first fastener component overlies at least a portion of said first surface of said fastener tab substrate.

5. A personal care article as in claim 2 wherein said first fastener component includes hook material.

6. A personal care article as in claim 1 wherein said fastener apparatus includes a first fastener component operable to make a fastening attachment to said landing zone, said landing zone comprising a non-woven fabric portion of said outer cover, said non-woven fabric portion being engageable with said first fastener component to provide an operable fastening attachment of said first fastener component to said landing zone.

7. A personal care article as in claim 6 wherein said fastener apparatus comprises:
   a first fastener component secured to a surface of said substrate at each laterally opposed end regions of one of said first and second waistband sections, said first fastener component being operable to make a fastening attachment to said landing zone.

8. A personal care article as in claim 7 wherein said landing zone comprises a non-woven fabric portion of said outer cover which is engageable with said first fastener component to provide an operable fastening attachment of said first fastener component to said landing zone.

9. A personal care article as in claim 1 wherein said absorbent structure includes a substantially liquid impermeable backsheet, a liquid permeable bodyside liner superposed on said backsheet, and an absorbent core disposed between said bodyside liner and said backsheet.

10. A personal care article as in claim 1 wherein said extendible attachment elements each have at least one pleat folded therein which creates said absorbent structure and said substrate.

11. A personal care article as in claim 1 wherein said grasping panel has a Gurley stiffness value of at least about 10 milligrams.

12. A personal care article as in claim 1 wherein said grasping panel has a Gurley stiffness value of less than about 10,000 milligrams.

13. A personal care article as in claim 1 wherein said grasping panel has a Gurley stiffness value of less than about 2,000 milligrams.

14. A personal care article as in claim 1 wherein the second waistband section is resiliently stretchable along the cross-direction.

15. A personal care article as in claim 1 wherein said bodyside liner is superposed over at least a portion of said outer cover.

16. A personal care article as in claim 1 wherein said grasping panel has a width of at least about 2 centimeters and a length of at least about 3 centimeters.

17. A personal care article having a lateral cross-direction and a lengthwise longitudinal direction, a front portion, a rear portion, and a crotch portion interconnecting said front and rear portions, said personal care article comprising:
   (a) an article substrate comprising an outer cover and a bodyside liner, at least about 30% of an area of said outer cover being resiliently stretchable, said outer cover having a first waistband section in the front portion and a second waistband section in the rear portion, at least one of said first waistband section and said second waistband section being resiliently stretchable along at least said cross-direction, said first waistband section having first laterally opposed end regions and said second waistband section having second laterally opposed end regions;

(b) an absorbent structure comprising an absorbent core disposed between said outer cover and said bodyside liner, said absorbent core being operable for receiving and storing exudates of a wearer of said personal care article;

(c) extendible attachment elements securing said absorbent structure to said outer cover while accommodating resilient stretching of said outer cover along the cross-direction, wherein said extendible attachment elements accommodate resilient stretching of at least one of said first waistband section and said second waistband section, of at least about 5% elongation, as determined with respect to an unstretched condition of the respective said waistband section;

(d) fastener apparatus disposed at each laterally opposed end region of one of said first and second waistband sections, configured to hold said personal care article on a wearer, said fastener apparatus comprising a first surface and an opposing second surface, said first surface of said fastener apparatus being disposed at the respective said laterally opposed end regions; and (e) first and second substantially non-stretchable non-fastening grasping panels disposed at said laterally opposed stretchable end regions of the other of said first and second waistband sections, whereby said non-stretchable grasping panels are attached to said substrate at portions of said substrate which are stretchable in the cross-direction, said second surface of said fastener apparatus being engageable to said resiliently stretchable area of said outer cover to thereby hold said personal care article on the wearer.

18. A personal care article as in claim 17 wherein said fastener apparatus on each said laterally opposed end region of one of said first and second waistband sections comprises:
    a fastener tab substrate having a first surface and a second surface; and
    a first fastener component secured to said first surface, said second surface of said fastener tab substrate being secured to at least a portion of said article substrate.

19. A personal care article as in claim 18 wherein at least a portion of said first fastener component extends outwardly from said fastener tab substrate.

20. A personal care article as in claim 18 wherein an entirety of said first fastener component overlies at least a portion of said first surface of said fastener tab substrate.

21. A personal care article as in claim 18, further comprising a resiliently stretchable landing zone, wherein said first fastener component is operable to make a fastening attachment to said resiliently stretchable landing zone, said landing zone comprising a non-woven fabric portion of said outer cover, engageable with said first fastener component to provide an operable fastening attachment of said first fastener component to said landing zone.

22. A personal care article as in claim 21 wherein said first fastener component includes hook material.

23. A personal care article as in claim 18 wherein said grasping panel has a Gurley stiffness value of less than about 2,000 milligrams.

24. A personal care article as in claim 18 wherein said grasping panel has a Gurley stiffness value of at least about 10 milligrams.

25. A personal care article as in claim 18 wherein the second waistband section is resiliently stretchable along the cross-direction.

26. A personal care article having a lateral cross-direction and a lengthwise longitudinal direction, a front portion, a rear portion, and a crotch portion interconnecting said front and rear portions, said personal care article comprising:

(a) an article substrate comprising an outer cover and a bodyside liner, wherein at least about 30% of an area of said outer cover is resiliently stretchable, said outer cover having a first waistband section in said front portion and a second waistband section in said rear portion, at least one of said first waistband section and said second waistband section being resiliently stretchable along at least said cross-direction, said first waistband section having first and second laterally opposed end regions and said second waistband section having third and fourth laterally opposed end regions;

(b) an absorbent structure comprising an absorbent core disposed between said outer cover and said bodyside liner, said absorbent core being operable for receiving and storing exudates;

(c) extendible attachment elements securing said absorbent structure to said outer cover while accommodating resilient stretching of said outer cover along the cross-direction, wherein said extendible attachment elements accommodate resilient stretching of at least one of said first waistband section and said second waistband section, of at least about 5% elongation, as determined with respect to an unstretched condition of the respective said waistband section;

(d) first and second fastener apparatuses, each said fastener apparatus comprising a first surface and an opposing second surface, respective said first surfaces of said first and second fastener apparatuses being irreleaseably affixed to respective said laterally opposed end regions of one of said first waistband section and said second waistband section, said second surface of each said fastener apparatus being releaseably engageable to thereby hold said personal care article on a wearer;

(e) a resiliently stretchable fastener landing zone for receiving and securing said first and second fastener apparatuses thereto, said landing zone being integral with the outer cover and disposed at a respective said waistband section free of said first and second fastener apparatuses, thus enabling engagement between said second surface of each said fastener apparatus and said landing zone; and (f) first and second substantially non-stretchable grasping panels disposed on, and extending outwardly from, any resiliently stretchable portion of said outer cover at respective said laterally opposed end regions of the waistband section not irreleaseably affixed to said first surface of each said fastener apparatus.

27. A personal care article as in claim 26 wherein each said grasping panel has a Gurley stiffness value of at least about 10 milligrams.

28. A personal care article as in claim 26 wherein said grasping panels are secured to respective said laterally opposed end regions.

29. A personal care article as in claim 26 wherein said landing zone comprises a nonwoven fabric portion of said outer cover which is engageable with said fastener apparatus to provide an operable fastening attachment thereto.

30. A personal care article as in claim 26 wherein a said fastener apparatus comprises:
  a fastener tab substrate having a first surface and a second surface; and
  a first fastener component secured to at least a portion of said first surface of said fastener tab substrate, at least a portion of said second surface being secured to at least a portion of said outer cover at a respective said laterally opposed end region, said first fastener component being operable to make a fastening attachment to said resiliently stretchable landing zone.

31. A personal care article as in claim 26 wherein at least a portion of said first fastener component extends outwardly from said fastener tab substrate.

32. A personal care article as in claim 30 wherein an entirety of said first fastener component overlies said first surface of said fastener tab substrate.

33. A personal care article as in claim 26 wherein said absorbent structure includes a substantially liquid impermeable backsheet and a liquid permeable bodyside finer superposed on said backsheet, said absorbent core being disposed between said bodyside liner and said backsheet.

34. A personal care article as in claim 26 wherein said second waistband section is resiliently stretchable along the cross-direction.

35. A personal care article as in claim 26, said bodyside finer being extensible and being superposed on said outer cover, wherein said absorbent structure is disposed between said bodyside liner and said outer cover.

* * * * *

UNITED STATES PATENT AND TRADEMARK OFFICE
CERTIFICATE OF CORRECTION

PATENT NO. : 7,018,368 B2
APPLICATION NO. : 10/145645
DATED : March 28, 2006
INVENTOR(S) : Paul T. Van Gompel et al.

It is certified that error appears in the above-identified patent and that said Letters Patent is hereby corrected as shown below:

Claim 1, column 15, line 26, delete "crass" and substitute --cross--

Claim 31, column 19, line 11, delete "26" and substitute --30--

Claim 33, column 20, line 3, delete "finer" and substitute --liner--

Claim 35, column 20, line 10, delete "finer" and substitute --liner--

Signed and Sealed this

Fifteenth Day of August, 2006

JON W. DUDAS
*Director of the United States Patent and Trademark Office*